US00PP12329P2

(12) United States Plant Patent
Utecht

(10) Patent No.: US PP12,329 P2
(45) Date of Patent: Jan. 1, 2002

(54) GERANIUM PLANT NAMED 'FISLUNOVA'

(75) Inventor: Angelika Utecht, Montabaur (DE)

(73) Assignee: Plorfis AG, Binningen (CH)

( * ) Notice: Subject to any disclaimer, the term of this patent is extended or adjusted under 35 U.S.C. 154(b) by 0 days.

(21) Appl. No.: 09/323,152

(22) Filed: Jun. 1, 1999

(51) Int. Cl.[7] ..... A01H 5/00
(52) U.S. Cl. ..... Plt./332
(58) Field of Search ..... Plt./332, 324

(56) References Cited

FOREIGN PATENT DOCUMENTS

| | | |
|---|---|---|
| PL | 467 | 12/1998 |
| CA | 98-1358 | 4/1998 |
| CH | 98-26-1422 | 4/1998 |
| DE | PEL 1358 | 9/1996 |
| EP | 97/0956 | 9/1997 |

OTHER PUBLICATIONS

Pelargonium 1998, Pelfi Fischer, Hillscheid Germany, p. 17 (1998/1999).
UPOV–ROM GTIM Computer Database 1999/02, GTI Jouve Retrieval Software, citation for 'Fislunova', 1996–1998.*
Licensing agreement, http://www.sicasov.com/baremes/f–fl9899.htm, 1998/1999.*#jf139##

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of geranium plant named 'Fislunova', as described and illustrated, and particularly characterized by the combined features of white, double flowers in compact, semi-spherically shaped inflorescence, medium green foliage with slight zonation, early to medium flowering response, and moderately compact plant habit.

2 Drawing Sheets

BACKGROUND OF THE INVENTION

The present invention comprises a new and distinct cultivar of geranium plant, botanically known as *Pelargonium peltatum*, and hereinafter referred to by the cultivar name 'Fislunova'.

'Fislunova' is a product of a planned breeding program which had the objective of creating white flowering cultivars with large flower heads and with a well-branched and only moderately vigorous growth habit.

'Fislunova' was originated from a hybridization made by the inventor, Angelika Utecht, in a controlled breeding program in Galder, Gran Canaria, Spain, in 1993. The female parent was the patented variety 'Fisbliz' (U.S. Plant Pat. No. 9,373), having single white flowers, medium green leaves with slight zonation, and vigorous growth. The male parent of 'Fislunova' was an unnamed hybrid derived from a cross between 'Fisbliz' and a self-seedling from 'Schneek önigin' (syn. 'Snow Queen'). The unpatented cultivar 'Schneekönigin' is characterized by large, double, white flowers, light to medium green foliage, and moderately vigorous growth.

'Fislunova' was selected as one flowering plant within the progeny of the stated cross by the inventor, Angelika Utecht, in the spring of 1994 in a controlled environment in Galdar, Gran Canaria, Spain.

The first act of asexual reproduction of 'Fislunova' was accomplished when vegetative cuttings were taken from the initial selection in the summer of 1994 in a controlled environment in Galder, Gran Canaria, Spain by Angelika Utecht. Horticultural examination of plants grown from cuttings of the clone initiated in May 1995 in Hillscheid, Federal Republic of Germany, and continuing thereafter, has demonstrated that the combination of characteristics as herein disclosed for 'Fislunova' are firmly fixed and are retained through successive generations of asexual reproduction.

BRIEF DESCRIPTION OF THE INVENTION

The following traits have been repeatedly observed and are determined to be basic characteristics of 'Fislunova', which in combination distinguish this geranium as a new and distinct clutivar:

1. Large, white, double flowers;
2. Compact, semi-spherically shaped inflorescence;
3. Medium-green foliage with slight zonation;
4. Moderately compact plant habit; and
5. Medium spring flowering response.

'Fislunova' has not been observed under all possible environmental conditions. The phenotype of the new cultivar may vary significantly with variations in environment such as temperature, light intensity and daylength without any change in genotype of the plant. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fislunova' are the patented variety 'Fisuna' (U.S. Plant Pat. No. 9,522) and the unpatented cultivar 'Scheekönigin', ( syn, 'Snow Queen'). Reference is made to Chart A which compares certain characteristics of 'Fislunova' to those same characteristics of 'Fisuna'.

CHART A

| | 'Fislunova' | 'Fisuna' |
|---|---|---|
| Diameter of flower | 58 mm | 49 mm |
| Color of markings of petals | RHS 66 B-C | RHS 74B |
| Diameter of umbel | 95 mm | up to 110 mm, variable |
| Length of peduncle | 168 mm | 219 mm |
| No. of branches | 5.0 | 4.2 |
| Length of plants (based on 10-week old plants) | 19.9 cm | 33.5 cm |
| Foliage: surface | Dull | Glossy |

In general comparison to 'Fisuna', 'Fislunova' has larger white florets with less tendency to develop a pink hue; rounder and more uniformly shaped umbels and shorter, but stronger, peduncles; and a more compact plant habit. Furthermore, the leaves of 'Fislunova' have less distinct and more rounded lobes. In comparison to 'Schneekönigin', 'Fislunova' has differeently shaped leaves with less distinctly developed lobes, and a more intense and more stable green foliage color.

BRIEF DESCRIPTION OF THE DRAWING

The accompanying color photographic drawings show typical flower and foliage characteristics of 'Fislunova' with colors being as true as possible will illustrations of this type.

FIG. 1 is a side view of the plant in a hanging basket.

FIG. 2 is a close-up view of the inflorescence of 'Fislunova'.

DETAILED BOTANICAL DESCRIPTION

The measurements were taken in Langley, British Columbia, Canada, on May 26, 1998—10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheid, Germany.

Classification:

*Botanical.*—A hybrid of the species *Pelargonium peltatum L'Hérit.*

*Commercial.*—Ivy geranium, cv. 'Fislunova'.

Inflorescence:

*Umbel.*—Shape: Semi-spherical. Average diameter: 95 mm. Average depth: 56 mm. Peduncle length: 168 mm. Peduncle color: Light green, RHS 143 C, no anthocyanin. Peduncle texture: Slightly rough with weak pubescence. Pedicel length: 25 mm. Pedicel color: Green, near RHS 143 A, infusion of anthocyanin may occur near the 'joint' of the pedicel. Number of flowers per umbel: Approximately 6–9. Lastingness of the individual umbel: 6–9 flowers or buds in various stages of development; the individual umbel lasts approximately 15 days in greenhouse conditions in spring at a temperature of 18° C.

*Corolla.*—Average diameter: 58 mm. Form: Double. Shape: Large, almost round, with broad upper petals. Average number of petals: 14.5. Number of petaloids: Up to 5. Color of petaloids: White, often with purple-pink stripes RHS 66 B–66 C. Color (general tonality from a distance of three meters): White, young flowers may have a slight pink shade. Color of upper petals: Pure white, RHS 155 D. Markings of upper petals: 2–4 purple-pink parallel stripes and a tiny macule in the middle of the petal, color is RHS 66 B–C. Color of lower surface petals: Pure white, RHS 155 D, usually without any markings. Color of lower surface of petals: Pure white, RHS 155 D, with purple-pink veins. Color of sepals: Green, RHS 144 A, occasionally with slight infusion of anthocyanin on the largest sepal, which can result in a brownish-green color, RHS 152 A, to a weakly rust-colored hue, RHS 173 B. Number of sepals: 5. Texture of sepals: Smooth, moderately hairy.

*Bud (just before petals unfold).*—Shape: Elliptical. Color (sepals): Light to medium-green, RHS 143 A–144 A. Color (petals): Cream to very light-pink, RHS 19 D–49 D, with purple lines. Length: Approximately 20 mm. Width: Approximately 12 mm.

*Reproductive organs.*—Androecium: Approximately 5 fertile anthers, white filaments, orange pollen. Gynoecium: 5–6-lobed pink to purple-pink stigma, RHS 65 A, and whitish style. Fertility/seed set: No spontaneous seed set observed.

*Spring flowering response period.*—In Hillscheid, Germany, in 1998, plants had on average 0.4 flowers opened 15 weeks after planting of unrooted cuttings.

*Outdoor flower production.*—Medium number of flowers, fair for a variety that develops relatively large inflorescence.

*Blooming habit.*—Continuous flowering from about May to mid-September; after which flowering may be poor depending on general conditions and light intensity. There is no noticeable fragrance.

*Durability.*—Good shatter resistance; average rain resistance.

Plant:

*Foliage.*—Form: Ivy-shaped with only weakly developed lobes and with closed to slightly overlapping base and with dull (not glossy) surface. Margin: Entire. Size of leaf: 72 mm wide. Texture: Surface flat, appears slightly rough and dull, due to weak pubescence. Color of upper surface: Medium green, approximately RHS 137 B. Color of lower surface: Medium to light-green, RHS 137 D. Color of zonation: Brown, approximately RHS 166 A, only weak, may disappear in summer. Tolerance of botrytis: Average.

*General appearance and form.*—Plant habit: Medium-sized, relatively compact and round, only weakly trailing. Internode length: 25–40 mm. Branching pattern: 5.0 naturally-occurring branches. Length of branches: 60 cm (in late August, based on 32-week-old plants).

I claim:

1. A new and distinct cultivar of geranium plant named 'Fislunova', as described and illustrated.

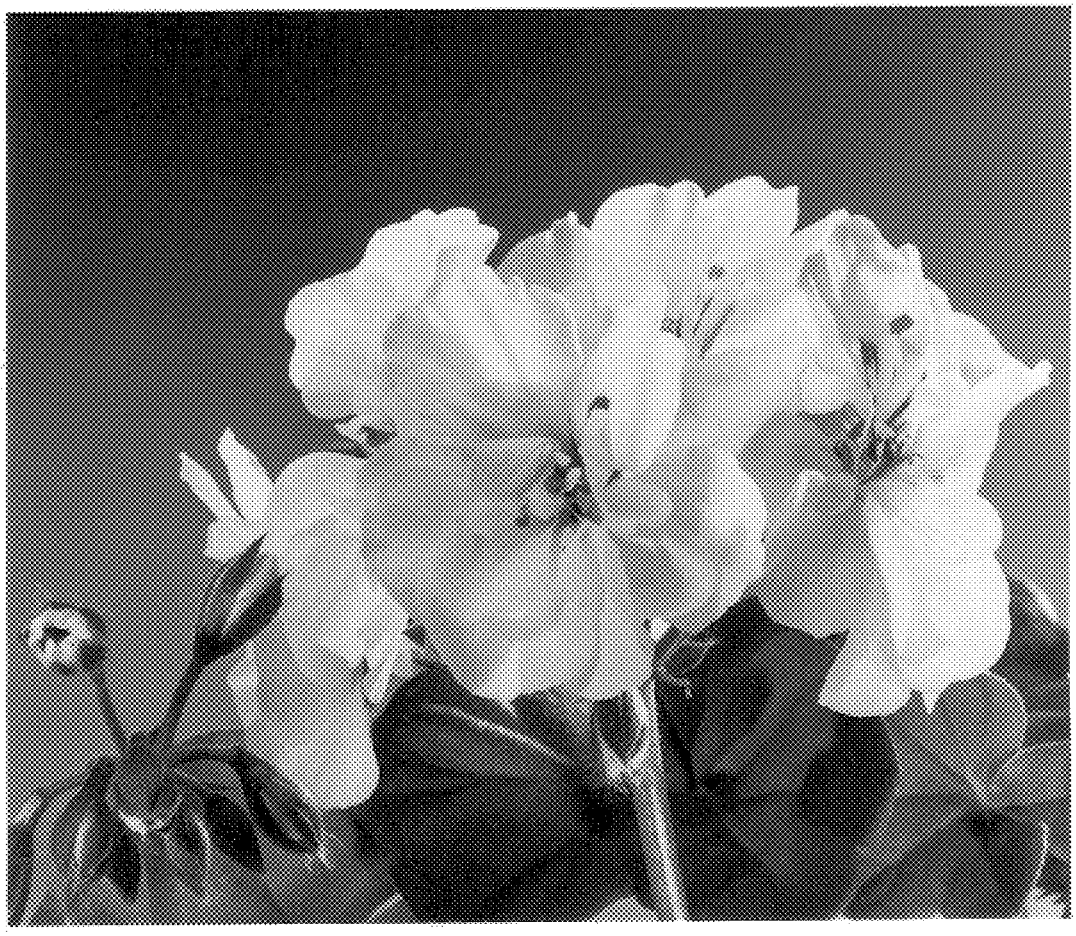

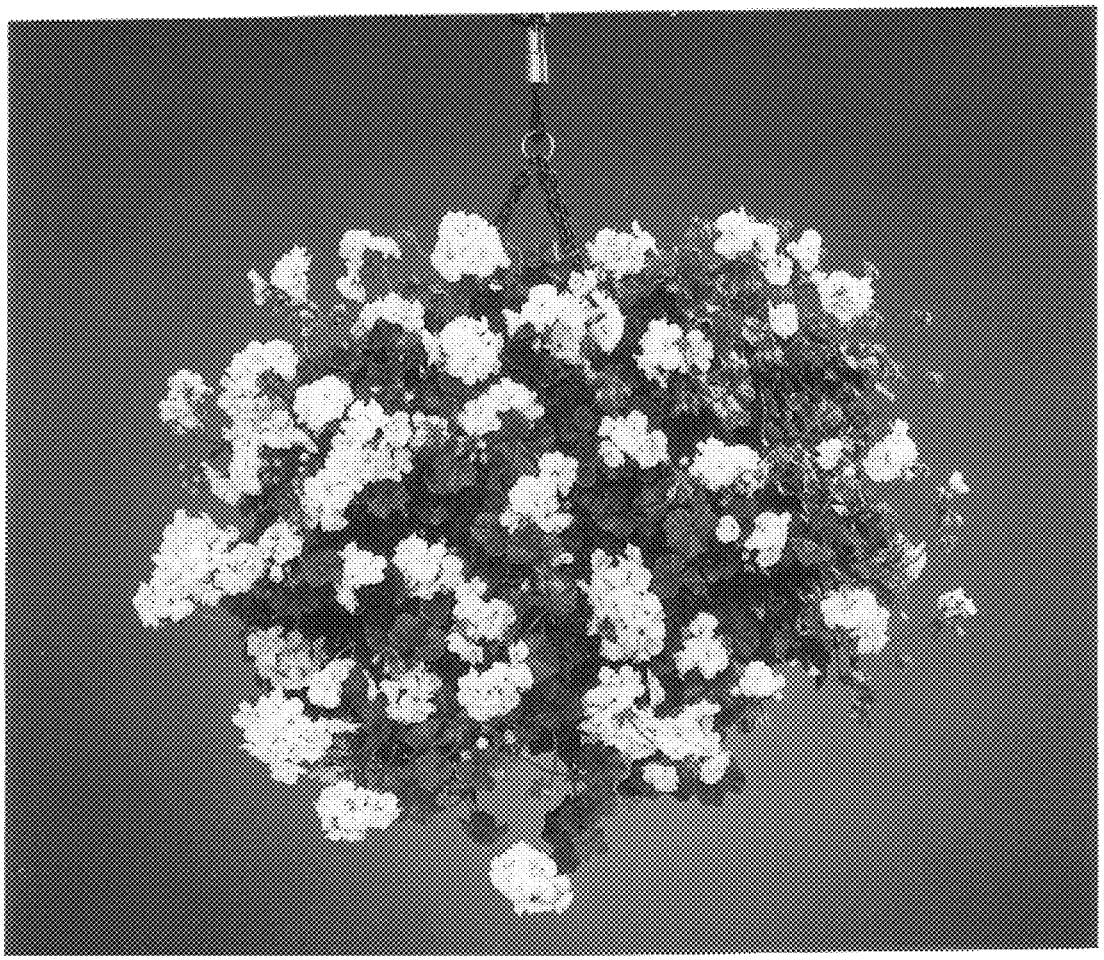

* * * * *